United States Patent [19]

Nemet-Mavrodin

[11] Patent Number: 4,808,295

[45] Date of Patent: Feb. 28, 1989

[54] TWO STAGE PROCESS FOR THE PRODUCTION OF A HIGH BENZENE AROMATIC PRODUCT

[75] Inventor: Margaret Nemet-Mavrodin, Cherry Hill, N.J.

[73] Assignee: Mobil Oil Corporation, New York, N.Y.

[21] Appl. No.: 133,773

[22] Filed: Dec. 16, 1987

Related U.S. Application Data

[63] Continuation-in-part of Ser. No. 89,194, Aug. 25, 1987.

[51] Int. Cl.$^4$ .................. C10G 35/06; G07C 12/00
[52] U.S. Cl. .................................. 208/65; 208/138; 585/412; 585/417; 585/419
[58] Field of Search .................. 208/65; 585/417, 419, 585/412

[56] References Cited

U.S. PATENT DOCUMENTS

| | | | |
|---|---|---|---|
| 3,756,942 | 9/1973 | Cattanach | 208/137 |
| 3,760,024 | 9/1974 | Cattanach | 260/673 |
| 4,180,689 | 12/1979 | Davies et al. | 585/415 |
| 4,304,686 | 12/1981 | Telford | 502/61 |
| 4,350,835 | 9/1982 | Chester et al. | 585/415 |
| 4,560,820 | 12/1985 | Field | 585/489 |

FOREIGN PATENT DOCUMENTS 0050021 4/1982 European Pat. Off. .

OTHER PUBLICATIONS

Hughes et al., "Aromatization of Hydrocarbons over Platinum Alkaline Earth Zeolites" in New Developments in Zeolite Science and Technology, Vol. 28, pp. 725–732, (1986).

Primary Examiner—Curtis R. Davis
Attorney, Agent, or Firm—Alexander J. McKillop; Charles J. Speciale; Dennis P. Santini

[57] ABSTRACT

A process is provided for converting a feedstock comprising a preponderant amount of $C_2$–$C_{10}$ aliphatic compounds to a product having a high proportion of benzene in a two stage process, with the effluent from the first stage passing directly to the second stage, i.e., with no intermediate processing such as purification or separation. In the first stage, the feedstock is contacted under suitable conversion conditions with a catalyst comprising an aluminosilicate zeolite having a Constraint Index in the approximate range of 1 to 12 and a degree of acidity indicated by an alpha value of at least about 3. The effluent from the first stage is then passed directly to a second stage where it is contacted under conversion conditions with a catalyst comprising platinum and a zeolite which either has a Constraint Index of approximately 1 to 12 or is a potassium zeolite L in which the number of protonic acid sites have been reduced by exchange with barium, strontium or calcium, the second stage zeolite being substantially non- or low-acid as indicated by an alpha value no higher than about 1.

9 Claims, No Drawings

TWO STAGE PROCESS FOR THE PRODUCTION OF A HIGH BENZENE AROMATIC PRODUCT

CROSS-REFERENCE TO RELATED APPLICATION

This application is a continuation-inpart of application Ser. No. 89,194 filed by applicant Aug. 25, 1987

BACKGROUND OF THE INVENTION

1. Field of the Invention

This invention relates to a two stage process for the production of aromatics having a particularly high proportion of benzene from $C_2$ to $C_{10}$ aliphatic hydrocarbons.

2. Background Information

It is known to use zeolites in the preparation of catalysts for the production of aromatic hydrocarbons from aliphatic hydrocarbons by passing the aliphatic hydrocarbon over the catalyst at an elevated temperature in the liquid or vapor phase. Zeolites of various types have been suggested for the preparation of such catalysts, e.g., ZSM-type zeolites containing any of various cations such as hydrogen, ammonium or metallic cations, e.g., gallium, or containing any of various metal oxides impregnated on its surface, e.g., a gallium oxide. However, while the yield of "BTX" aromatic fractions, i.e., consisting of benzene, toluene, xylenes and ethylbenzene, using the foregoing processes, may be relatively high, the yields of benzene alone, which is a particularly valuable feedstock for chemical processes, are fairly low. Thus, any means to increase the yield of benzene from aliphatic feedstocks, e.g., raffinates from aromatics extraction processes, is highly desirable.

3. Information Disclosure Statement

The following information is disclosed in accordance with the terms of 37 CFR 1.56, 1.97 and 1.98.

U.S. Pat. Nos. 3,756,942 and 3,760,024, disclose the preparation of aromatic compounds from aliphatic compounds using as catalyst a ZSM-type zeolite in which at least some of the original cations have been replaced by hydrogen, ammonium or metallic cations, or impregnated with a metallic component as described previously.

U.S. Pat. Nos. 4,180,689, 4,304,686, 4,350,835 and European Patent Specification Publication No. 50,021 each discloses a process of converting aliphatic compounds to aromatics utilizing as catalyst a zeolite, e.g., ZSM-5, containing gallium in impregnated or cation exchanged form.

The foregoing and similar prior art disclosures emphasize the conversion of aliphatics to aromatics broadly, or, in some cases, to the "BTX" fraction of aromatics composed of benzene, toluene and $C_8$ aromatics, to be used, for example, as a high octane gasoline blending component. However, there is generally no suggestion in such disclosures of the desirability of maximizing the production of benzene, specifically, e.g., for use as a chemical feedstock.

U.S. Pat. No. 4,560,820 teaches a process of dealkylating alkylaromatic hydrocarbons, e.g., toluene to produce benzene, using intermediate pore size zeolites substantially free of acidity. However, there is no suggestion in this patent of the application of the process to a feedstock which already contains a substantial proportion of benzene.

Hughes et al., "Aromatization of Hydrocarbons Over Platinum Alkaline Earth Zeolites," in New Developments in Zeolite Science and Technology, Vol. 28, pp. 725-732, teach platinum-containing alkaline earth exchanged alkali metal Zeolite L, e.g., platinum containing barium-exchanged potassium zeolite L (Pt/BaKL), used as a catalyst for the aromatization of paraffins. There is, however, no disclosure by this reference of the conversion of any feedstock which already contains a substantial proportion of aromatics such as benzene.

SUMMARY OF THE INVENTION

In accordance with the invention, a feedstock comprising a preponderant amount of $C_2$-$C_{10}$ aliphatic compounds is converted to a product having a high proportion of benzene in a two stage process, with the effluent from the first stage passing directly to the second stage, i.e., with no intermediate processing such as purification or separation. In the first stage, the feedstock is contacted under suitable conversion conditions with a catalyst comprising an aluminosilicate zeolite having a Constraint Index as hereinafter defined of approximately 1 to 12 and a degree of acidity indicated by an alpha value as hereinafter defined of at least about 3. The effluent from the first stage is passed directly to a second stage where it is contacted under conversion conditions with a catalyst comprising platinum and a zeolite which either has a Constraint Index of approximately 1 to 12, or is a potassium form of zeolite L in which at least some of the cations are exchanged with barium, strontium or calcium, the second stage zeolite being substantially non- or low-acid as indicated by an alpha value no higher than about 1.

DESCRIPTION OF SPECIFIC EMBODIMENTS

The zeolite used in producing the first stage catalyst of this invention, may be prepared by any of the methods known in the art. Thus, variations of the original method for the production of this type of zeolite utilizing an "organic template" provided by the presence of organic cations, are disclosed in U.S. Pat. Nos. 3,702,886 and Re. 29,948, and European Patent Application No. 130,809. Alternatively, the zeolite may be prepared without employing any organic cations, but utilizing instead seeds of the desired zeolite in the formulating mixture which seeds themslves were formed in the presence of organic ions or from other seeds formed in the presence of organic ions, etc. as disclosed, for example, in U.S. Pat. Nos. 4,175,114; 4,199,556; and 4,351,748. Moreover the contemplated zeolites may be formed in the absence of any organic ions or seeds of the type described, utilizing instead as precursor a silica or aluminosilicate which is precipitated or crystallized from solution or homogenous amorphous phase and having certain characteristics, as disclosed for example in pending application Ser. No. 014,147, filed Feb. 12, 1987, or European Patent Application No. 106,552, the entire disclosures of which are incorporated by reference. Other methods for the preparation of the desired zeolites, i.e. zeolites having X-ray diffraction patterns typical of such zeolites, are disclosed in the art and may also be used. In general, the zeolite is preferably prepared using any of the foregoing methods so that the silica/alumina molar ratio of the as synthesized zeolite is in the range of about 25 to about 1000.

Ion exchange of the first stage zeolite can be conducted to effect ammonium exchange at its cationic sites. The source of the ammonium ions is not critioal; thus the source can be ammonium hydroxide or an ammonium salt such as ammonium nitrate, ammonium sulfate, ammonium chloride and mixtures thereof. These reagents are usually in aqueous solutions, e.g., of one normal concentration, and ammonium exchange may be conducted in multiple stages. Calcination of the ammonium exchanged zeolite at a temperature, for example, of up to 600° C., will produce the zeolite in its acid, i.e., "H" or protonated form, contemplated for use in the process of this invention.

The process of the present invention may be carried out using a first stage catalyst in which a metallic element is impregnated on the surface of the acid form of the zeolite or is ion-exchanged with some of the original cations or ammonium or hydrogen ions of the zeolite using techniques of impregnation or ion-exchange which are well-known in the art. For example, the metallic element may be impregnated on the surface of the zeolite by preparing a solution, e.g., an aqueous solution of the metallic element compound such as the nitrate and adding to this solution a preshaped form of the desired zeolite such as 14/25 mesh particles with or without a binder, or in the form of a fluid bed powder, and allowing the zeolite to be thoroughly contacted with the solution. The contacted catalyst is then dried at a moderate temperature, e.g., 100 to 120° C. After calcination, e.g., at 538° C., the zeolite contains the metallic element impregnated on its surface in the form of the metal oxide.

The metallic element in the catalyst composition is present as ions if some cations in the aluminosilicate support have been exchanged with metal ions. In this case, the metal ions are suitably provided as an aqueous solution of a salt such as for instance, the sulfate, nitrate, or chloride. Such catalysts may be produced by conventional ion exchange techniques and the catalysts so produced are subsequently dried. For example, an aqueous solution of a soluble metal compound such as the nitrate may be placed in contact with the ammonium form of a preshaped form of the zeolite at ambient or elevated temperature, e.g., by refluxing. The exchanged zeolite is then separated by decantation followed by filtration, washed several times with deionized water and finally dried.

When the catalyst composition is prepared by using a compound of a metal which ionizes in aqueous solution, for example, the nitrate, some of the ions are generally exchanged with the cations in the zeolite even if the preparation was directed to impregnation.

Whichever method of catalyst preparation is used, the amount of metallic element present in the total catalyst composition, if used, may vary, for example, between about 0.5 and 5 percent by weight, preferably between about 0.5 and 2.0 percent by weight. Metallic elements which may be present in impregnated form or as replacing cations are one of more of various suitable metals in Groups I through VIII of the Periodic Table including by way of example gallium (which is preferred), zinc, platinum, rhenium, cobalt, titanium, tellurium, sodium, nickel, chromium, aluminum, copper, palladium, tin, iron, calcium, manganese, magnesium, cadmium, aluminum and rare earth metals or other modifiers, such as phosphorus, or a combination of any of these.

A particularly preferred first stage catalyst is a zeolite of the type described loaded with, e.g., about 0.5 to 5 wt. %, preferably from about 0.5 to 2 wt. % of gallium, with the gallium loaded zeolite having been calcined at a temperature of at least about 700° C., preferably from about 800° to 825° C., for a period of about 1 to 1.5 hours before being used as a catalyst. This catalyst is described in greater detail in parent application Ser. No. 89,194, filed Aug. 25, 1987, the entire disclosure of which is incorporated by reference.

The silica/alumina ratio of the catalyst may be determined by conventional analysis. This ratio is meant to represent, as closely as possible, the ratio in the rigid anionic framework of the zeolite crystal and to exclude aluminum in the binder or in cationic or other form within the channels. As synthesized ZSM-5 zeolites having silica/alumina molar ratios in the contemplated range, e.g., about 25 to 1000, may be modified to higher silica/alumina molar ratios by decreasing the aluminum content of the zeolites by steaming, dealuminizing or framework exchange procedures.

The members of the class of zeolites useful herein have an effective pore size of generally about 5 to about 8 angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites which provide relatively free access to the internal zeolite structure have a low value for the Constraint Index, and usually pores of large size, e.g., greater than 8 angstroms. The method by which Constraint Index is determined is described fully in U.S. Pat. No. 4,016,218, incorporated herein by reference for details of the method.

Constraint Index (CI) values for some typical materials are:

|  | CI (at test temperature) | |
| --- | --- | --- |
| ZSM-4 | 0.5 | (316° C.) |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |
| ZSM-34 | 50 | (371° C.) |
| ZSM-35 | 4.5 | (454° C.) |
| ZSM-38 | 2 | (510° C.) |
| ZSM-48 | 3.5 | (538° C.) |
| ZSM-50 | 2.1 | (427° C.) |
| TMA Offretite | 3.7 | (316° C.) |
| TEA Mordenite | 0.4 | (316° C.) |

| | CI (at test temperature) | |
|---|---|---|
| Clinoptilolite | 3.4 | (510° C.) |
| Mordenite | 0.5 | (316° C.) |
| REY | 0.4 | (316° C.) |
| Amorphous Silica-alumina | 0.6 | (538° C.) |
| Dealuminized Y | 0.5 | (510° C.) |
| Erionite | 38 | (316° C.) |
| Zeolite Beta | 0.6–2.0 | (316° C.–399° C.) |

The above-described Constraint Index is an important and even critical definition of those zeolites which are useful in the preparation of the first stage catalyst of instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence of absence of binders. Likewise, other variables, such as crystal size of the zeolite, the presence of occluded contaminants, etc. may affect the Constraint Index. Therefore, it will be appreciated that it may be possible to so select test conditions, e.g., temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of interest herein with the approximate range of 1 to 12.

The class of zeolites defined herein as suitable for preparation of the first stage catalyst is exemplified by ZSM-5, ZSM-11, ZSM-12, ZSM-23, ZSM-35, ZSM-38, ZSM-48, and other similar materials. The compositions, methods of preparation, and X-ray diffraction patterns of these zeolites are typified in the following patents: ZSM-5 in the U.S. Pat. Nos. 3,702,886, Re. 29,948 and 4,061,724; ZSM-11 in U.S. Pat. No. 3,709,979; ZSM-12 in U.S. Pat. No. 3,832,449; ZSM-23 in U.S. Pat. No. 4,076,842; ZSM-35 in U.S. Pat. No. 4,016,245; ZSM-38 in U.S. Pat. No. 4,046,859 and ZSM-48 in U.S. Pat. No. 4,350,835. The entire disclosures of these patents are incorporated by reference insofar as their disclosures are necessary to identify the respective zeolites.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts prepared in the manner described, wherein the mole ratio of silica to alumina is at least about 25 and may be as high as about 1000 as synthesized. The incorporation of the identified patents should therefore not be construed as limiting the disclosed crystalline zeolites to those having the specific silica/alumina mole ratios discussed therein, it now being known that such zeolites may have higher silica/alumina ratios and yet, having the same crystal structure as the disclosed materials, may be useful or even preferred in some applications. It is the crystal structure, as identified in the X-ray diffraction "fingerprint", which establishes the identity of the specific crystalline zeolite material.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. Therefore, the preferred zeolites useful with respect to this invention are those having a Constraint Index as defined above of about 1 to about 12, a silica to alumina mole ratio of at least about 25 and up to about 1000 as synthesized and a dried crystal density of not less than about 1.6 grams per cubic centimeter. The dry density for known structures may be calculated from the number of silicon plus aluminum atoms per 1000 cubic angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968).

When the crystal structure is unknown, the crystal framework density may be determined by classical pyconometer techniques. For example, it may be determined by immersing the dry hydrogen form of the zeolite in an organic solvent which is not absorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| | Void Volume | Framework Density |
|---|---|---|
| Ferrierite | 0.28 cc/cc | 1.76 g/cc |
| Mordenite | .28 | 1.7 |

-continued

|  | Void Volume | Framework Density |
|---|---|---|
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

In utilizing the catalyst contemplated by this invention, it may be advantageous to incorporate the zeolite, prepared in the prescribed manner, with a matrix comprising another material resistant to the temperature and other conditions employed in the process. Such matrix material is useful as a binder and imparts greater resistance to the catalyst for the severe temperature, pressure and reactant feed stream velocity conditions encountered in many conversion processes.

Useful matrix materials included both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin amilies, which families include the sub-bentonites and the kaolins commonly known as Dixie, McNamee-Georgia and Florida clays or others in which the main mineral constituent is halloysite, kaolinite, kickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alimina, silica-magnesia, silica-zirconia, silica-thoria, silica-beryllia, and silica-titania, as well as ternary compositions, such as silica-alumina-thoria, silica-alumnina-zirconia, silica-aluninamagnesia and silica-magnesia-zirconia. The matrix may be in the form of a cogel. The relative proportions of zeolite component and inorganic oxide gel matrix, on an anhydrous basis, may vary widely, with the zeolite content ranging from between about 1 to about 99 percent by weight and more usually in the range of about 25 to about 65 percent by weight of the dry composite.

As stated, the first stage catalyst comprises an aluminosilicate zeolite which, in addition to having a CI in the approximate range of 1 to 12, also has some degree of acidity as indicated by an alpha value of at least 3. There is no critical upper limit of alpha value which is, however, determined for a particular zeolite when all its cationic sites are occupied by hydrogen ions. As is known in the art, the acid catalytic activity of a zeolite may be measured by its alpha value, which is the ratio of the rate constant of a test sample for cracking normal hexane to the rate constant of a standard reference catalyst, i.e. an amorphous silica alumina catalyst of 46 AI (Acidity Index). Thus, an alpha value=1 means that the test sample and the standard reference have about the same activity. The alpha test is described in U.S. Pat. No. 3,354,078 and in *The Journal of Catalysis*, Vol IV, pp. 527-529 (August 1965), each incorporated herein by reference as to that description. The relationship of alpha value to the intrinsic rate constants of other acid-catalyzed reactions is detailed in *Nature*, Vol 309, pp.589-591, 14 June 1984, incorporated herein by reference as to that detail.

The alpha value of a zeolite in general depends on its silica/alumina ratio which is inversely proportional to its alpha value, and the nature of its cations, with hydrogen ions tending to raise the alpha value and alkali metal ions tending to lower it. In general the zeolites hereinbefore described will have sufficient acidity for preparation of the first stage catalyst if at least part of its original alkali metal cations have been exchanged with hydrogen or ammonium ions. Alternatively, zeolites with too high a silica/alumina ratio and too low an alpha value can be activated with external alumina by impregnation/calcination to increase its alpha value to at least 3.

As stated, the second stage catalyst comprises platinum and a zeolite which may be either of two types: (1) a zeolite having a Constraint Index in the approximate range of 1 to 12; or (2) a potassium zeolite L exchanged with barium, strontium or calcium, such second stage zeolite being non- or low acid as indicated by an alpha value no greater than 1. The first type of zeolite may be of the same class as that contemplated for the first stage, as hereinbefore defined except that in view of its non- or low acidity, there is no upper limit on the silica/alumina ratio which may approach infinity, i.e., contain substantially no alumina as suggested in U.S. Pat. No. 4,061,724. However, even when a source of aluminum is not deliberately used in the preparation of the zeolite such as ZSM-5, because of the usual association of alumina with natural sources of silica, the silica/alumina ratio in the as synthesized zeolite will often be below 1000.

In general, zeolites having a CI in the approximate range of 1 to 12 and a silica/alumina ratio of at least about 14,000 as synthesized, have alpha values of no higher than about 1 as required for the preparation of the second stage catalyst. However, even when the as synthesized zeolite has an alpha value greater than 1, e.g., has a silica/alumina ratio as synthesized below about 14,000, e.g. as low as 25, the alpha value can often be reduced to no higher than about 1 by various procedures known in the art, e.g., steaming at a temperature of about 700° to 1300° F. for a period of about 0.5 to 20,000 hours, calcining in air at a temperature of about 800° to 1000° C. for a period of about 1 to 10 hours, or various framework exchange procedures to remove some aluminum. Alternatively, the acidity and thus the alpha value of the zeolite may be reduced by preserving all or some of the original alkali metal ions used in the preparation of the zeolite on the cationic sites or exchanging some of the cations present, e.g., ammonium ions, with alkali metal ions, e.g., sodium or potassium ions. Platinum is present, e.g., in an amount of about 0.1 to 1.0 wt. % based on the catalyst either due to its presence in the hydrothermal crystallization mixture or by subsequently loading the zeolite using techniques of impregnation and/or ion exchange, as desribed previously for the addition of metallic elements to the zeolite of the first stage catalyst.

The second type of second stage catalyst is based on zeolite L which is known in the art as disclosed, for example in Belgian Pat. No. 575,117 and D. W. Breck, "Zeolite Molecular Sieves", Wiley, New York, 1974, pp. 13–116. The catalyst suitable for use in the second stage reaction is prepared by first exchanging the potassium form of zeolite L with barium, strontium, or calcium, with barium preferred, in order to further reduce the number of protonic acid sites, as measured by adsorption of a suitable basic compound. This is followed by addition of platinum. The platinum may be added using ion exchange or impregnation techniques, and any of various solutions of soluble forms of platinum, as described previously for the addition of metallic elements to a contemplated zeolite in connection with the preparation of first stage catalyst.

The barium, strontium or calcium, may be added for example, by ion exchange with an aqueous solution of the nitrate salt followed by drying at 120° C. and calcination in air at a temperature of at least 150° C. Platinum is then added in an amount, for example, of about 0.1 to 1.0 wt. %, e.g., 0.8 wt. %, by incipient wetness impregnation with an aqueous solution of platinum (II) tetraamine nitrate. The technique is described in greater detail in the previously cited Hughes et al. article, the portions of which relating to the preparation of the catalyst are incorporated herein by reference.

The feed stream to the first stage of the process of this invention contains at least 50% by weight of at least one aliphatic hydrocarbon containing 2 to 10 carbon atoms. The hydrocarbon may be straight chain, open or cyclic and may be saturated or unsaturated. Some contemplated hydrocarbons are propane, propylene, n-butane, n-butenes, isobutane, isobutene, and straight- and branch-chain and cyclic pentanes, pentenes, hexanes, hexenes, heptanes, heptenes, octanes, octenes, nonanes, nonenes, decanes and decenes. A particularly preferred feedstock is the raffinate remaining after the extraction of aromatics from a reformed refinery stream and containing over 90 wt. % non-aromatics and over 50 wt. % of $C_5$–$C_7$ paraffins.

The first stage of the process is conducted so that the feed containing a high percentage of aliphatic hydrocarbons as defined is contacted with a first stage catalyst of this invention in the first stage reaction zone, under effective conversion conditions. In a typical embodiment of the process of this invention, the feed stream is introduced into the first stage reaction zone at a temperature within the range of about 450° C. to 700° C., a pressure within the range of about one atmosphere to 1000 psig, and a WHSV of about 0.1 to 50.

The effluent from the first stage is passed without any intermediate chemical, purification or separation treatment directly to a second stage reaction zone where it is contacted with a second stage catalyst which is one of the two types of platinum-containing catalysts as described under conversion conditions suitable for the dealkylation of alkyl benzenes to benzenes. Typical conditions are, for example, a temperature of about 450° to 595° C., a pressure in the range of about one to 30 atmospheres, and a WHSV of about 1 to 50.

The effluent from the second stage reaction zone is separated and distilled to remove desired aromatic product, e.g., benzene, and the remainder is recycled for further reaction.

The process of this invention may be carried out with the catalyst in each stage in the form of a fixed, moving, or fluidized bed.

The following examples further illustrate the invention. The "Example" is an embodiment of the two stage process of the invention, while the "Comparative Example" is an embodiment of a one stage process utilizing conditions similar to those of the first stage of the Example.

EXAMPLE

To prepare the first stage catalyst, ten grams of a zeolite composition comprising 25 wt. % of a ZSM-5 zeolite having a silica/alumina molar ratio of 55:1 and prepared as described in European Patent Application No 130,809, the entire disclosure of which is incorporated by reference, and 75 wt. % of kaolin as a binder, are calcined in air to 500° C. for 5 hours to remove any residual organic matter. This "unloaded zeolite" is then exchanged with 50 ml. of 0.5M aqueous ammonia solution at 90° C. for 4 hours, washed with deionized water, and again exchanged with the same ammonia solution overnight at room temperature. After this, the zeolite is again washed with deionized water, dried under vacuum, and exchanged with 30 ml. of 0.35M aqueous $Ga(NO_3)_3$ solution as described and again washed with deionized water as described. This gallium-exchanged zeolite is dried under 74 mm. Hg vacuum at 90° C. overnight and calcined in air at 500° C. in a muffle furnace for 5 hours to obtain a gallium-loaded, ZSM-5 zeolite catalyst containing 1.94% of gallium based on the weight of the catalyst. Before use, the catalyst is calcined in flowing air at 800° C. for one hour. The final catalyst has an alpha value of at least about 10.

The second stage catalyst is based on a high silica ZSM-5 having a silica/alumina mole ratio of about 892 and a sodium content of about 4.12 wt. %. The catalyst also contains 0.45 wt. % of platinum due to the presence of a soluble platinum component in the hydrothermal crystallization mixture used to prepare the zeolite. The second stage catalyst is of low acidity as indicated by an alpha value of below 1.

The feedstock is a Udex raffinate remaining after the extraction of aromatics from a reformed refinery stream and having the following composition:

| Component | Wt. % |
|---|---|
| $C_4$ Aliphatics | 0.1 |
| $C_5$ Aliphatics | 4.7 |
| $C_6$ Paraffins | 51.4 |
| $C_6$ Olefins & Naphthenes | 3.4 |
| $C_7$ Paraffins | 32.3 |
| $C_7$ Olefins & Naphthenes | 0.3 |
| $C_8$ Aliphatics | 1.2 |
| $C_9^+$ Aliphatics | 2.3 |
| Benzene | 0.2 |
| Toluene | 4.0 |
| Xylenes | 0.1 |

The feed stream enters a first stage reaction zone where it is passed over a bed of first stage catalyst at a temperature of 550° C., atmospheric pressure and a WHSV including binder of 0.63. The effluent from the first stage passes directly into a second stage reaction zone where it is contacted with a fixed bed of second stage catalyst at a temperature of 538° C., atmospheric pressure and a WHSV of 0.5. The yield of various components of the product effluent in terms of wt. % of feedstock aromatizables (aliphatic compounds) is as follows:

| | |
|---|---|
| Toluene | 9.5 |
| Benzene | 29.3 |
| $C_8$ Aromatics | 12.9 |
| $C_9^+$ Aromatics | 7.6 |
| $C_2$–$C_5$ Olefins | 5.1 |

COMPARATIVE EXAMPLE

The conditions of the first stage of the foregoing "Example" are utilized except that the reaction temperature is 600° C. and the WHSV is 0.66. No second stage is used. The yield of various components in terms of wt. % of feedstock aromatizables is as follows:

| | |
|---|---|
| Toluene | 22.5 |
| Benzene | 19.7 |
| $C_8$ Aromatics | 11.8 |
| $C_{9+}$ Aromatics | 9.7 |
| $C_2$–$C_5$ Olefins | 5.9 |

The results of the Example and Comparative Example illustrates that the yield of benzene can be increased using the two stage process of this invention over that which can be obtained from a one stage aromatization process similar to the first stage of the disclosed two stage process.

I claim:

1. A process for producing aromatic compounds containing a high proportion of benzene which comprises passing a feed containing at least 50 weight percent of $C_2$ to $C_{10}$ aliphatic hydrocarbons to a first stage reaction zone where it is contacted under conversion conditions with a catalyst comprising an aluminosilicate zeolite characterized by a Constraint Index within the approximate range of 1 to 12 and a degree of acidity indicated by an alpha value of at least 3, and passing the effluent from the first stage reaction zone directly to a second stage reaction zone where it is contacted under conversion conditions with a catalyst comprising platinum and either a zeolite having a Constraint Index in the approximate range of 1 to 12, or a potassium form of zeolite L in which the number of protonic acid sites have been reduced by exchange with barium, strontium or calcium, said second stage catalyst having a low degree of acidity as indicated by an alpha value of no higher than about 1.

2. The process of claim 1 wherein the zeolite of said first stage catalyst is a ZSM-5.

3. The process of claim 2 wherein said ZSM-5 has an as synthesized silica/alumina ratio of about 25 to 1000.

4. The process of claim 3 wherein said ZSM-5 has gallium loaded therein in an amount of about 0.5 to 5% based on the weight of the catalyst.

5. The process of claim 4 wherein said gallium loaded ZSM-5 is calcined at a temperature of at least about 700° C.

6. The process of claim 5 wherein said calcining is carried out at a temperature of about 800° to 825° C. for a period of about 1 to 1.5 hours.

7. The process of claim 1 wherein said second stage catalyst comprises a zeolite having a Constraint Index in the approximate range of about 1 to 12, and an as synthesized silica/alumina ratio of at least about 25, and about 0.1 to 1.0% of platinum, based on the weight of the catalyst.

8. The process of claim 1 wherein said second stage catalyst comprises a potassium form of zeolite L in which the number of protonic acid sites has been reduced by exchange with barium ions, and about 0.1 to 1.0% of platinum based on the weight of the catalyst.

9. The process of claim 1 wherein the conversion conditions of said first stage reaction zone include a temperature of from about 450° C. to about 700° C., a pressure of from about one atmosphere to about 1000 psig, and a EHSV of from about 0.1 to about 50, and the conversion conditions of said second stage reaction zone include a temperature of about 450° to 595° C., a pressure of about one to 30 atmospheres, and a WHSV of about 1 to 50.

* * * * *

UNITED STATES PATENT AND TRADEMARK OFFICE
CERTIFICATE OF CORRECTION

PATENT NO.    : 4,808,295

DATED         : February 28, 1989

INVENTOR(S)   : M. Nemet-Mavrodin

It is certified that error appears in the above-identified patent and that said Letters Patent is hereby corrected as shown below:

| | |
|---|---|
| Col. 1, line 7 | "impart" should be --in-part-- |
| Col. 2, line 45 | "themslves" should be --themselves-- |
| Col. 2, line 67 | "critioal" should be --critical-- |
| Col. 5, line 20 | "of" (first instance) should be --or-- |
| Col. 6, line 2 | "disoussed" should be --discussed-- |
| Col. 7, line 35 | "amilies" should be --families-- |
| Col. 8, line 4 | "Catalvsis" should be --Catalysis-- |
| Col. 8, line 68 | "desribed" should be --described-- |
| Col. 9, line 7 | "pp. 13-116" should be --pp. 113-116-- |
| Col. 10, line 66 | "atmosperhic" should be --atmospheric-- |
| Col. 12, claim 9, line 37 | "EHSV" should be --WHSV-- |

Col. 6, line 3, "oontemplates" should be --contemplates--.

Signed and Sealed this

Nineteenth Day of December, 1989

*Attest:*

JEFFREY M. SAMUELS

*Attesting Officer*    *Acting Commissioner of Patents and Trademarks*